(12) United States Patent
Ajima

(10) Patent No.: US 11,653,843 B2
(45) Date of Patent: May 23, 2023

(54) ELECTRONIC DEVICE AND ESTIMATION SYSTEM

(71) Applicant: KYOCERA Corporation, Kyoto (JP)

(72) Inventor: Hiromi Ajima, Kawasaki (JP)

(73) Assignee: KYOCERA Corporation, Kyoto (JP)

( * ) Notice: Subject to any disclaimer, the term of this patent is extended or adjusted under 35 U.S.C. 154(b) by 491 days.

(21) Appl. No.: 16/312,910

(22) PCT Filed: Jun. 13, 2017

(86) PCT No.: PCT/JP2017/021859
§ 371 (c)(1),
(2) Date: Dec. 21, 2018

(87) PCT Pub. No.: WO2018/003491
PCT Pub. Date: Jan. 4, 2018

(65) Prior Publication Data
US 2019/0216337 A1  Jul. 18, 2019

(30) Foreign Application Priority Data
Jun. 28, 2016 (JP) .............................. JP2016-127509

(51) Int. Cl.
*A61B 5/02* (2006.01)
*A61B 5/00* (2006.01)
(Continued)

(52) U.S. Cl.
CPC ................ *A61B 5/022* (2013.01); *A61B 5/00* (2013.01); *A61B 5/02* (2013.01); *A61B 5/0285* (2013.01);
(Continued)

(58) Field of Classification Search
CPC ....... A61B 5/022; A61B 5/02; A61B 5/02438; A61B 5/681; A61B 5/14532; A61B 5/14546; A61B 5/0285
See application file for complete search history.

(56) References Cited

U.S. PATENT DOCUMENTS 7,082,419 B1 * 7/2006 Lightowler ............ G06N 3/063
706/15
2002/0188210 A1  12/2002 Aizawa
(Continued)

FOREIGN PATENT DOCUMENTS

DE    202004007139 U1 * 7/2004 ........... A61B 5/1116
EP    1743576 A1 * 1/2007 ........... A61B 5/6838
(Continued)

OTHER PUBLICATIONS

Schram MT, Henry RM, van Dijk RA, Kostense PJ, Dekker JM, Nijpels G, Heine RJ, Bouter LM, Westerhof N, Stehouwer CD, Increased central artery stiffness in impaired glucose metabolism and type 2 diabetes: the Hoorn Study, Feb. 2004, Hypertension, 43(2):176-81. (Year: 2004).*

*Primary Examiner* — Christian Jang
(74) *Attorney, Agent, or Firm* — Studebaker & Brackett PC

(57) ABSTRACT

An electronic device includes a sensor configured to acquire a subject's pulse wave, a blood pressure measurement portion configured to measure the subject's blood pressure level, and a controller configured to estimate a state of glucose metabolism or lipid metabolism of the subject on the basis of an index based on the subject's pulse wave acquired by the sensor and the subject's blood pressure level measured by the blood pressure measurement portion.

10 Claims, 15 Drawing Sheets

(51) Int. Cl.
*A61B 5/145* (2006.01)
*A61B 5/022* (2006.01)
*A61B 5/024* (2006.01)
*A61B 5/0285* (2006.01)

(52) U.S. Cl.
CPC ...... *A61B 5/02438* (2013.01); *A61B 5/14532* (2013.01); *A61B 5/681* (2013.01)

(56) References Cited

U.S. PATENT DOCUMENTS

| | | | |
|---|---|---|---|
| 2003/0004421 A1* | 1/2003 | Ting | A61B 5/021 600/485 |
| 2008/0275317 A1 | 11/2008 | Cho et al. | |
| 2012/0059237 A1* | 3/2012 | Amir | A61B 5/0285 600/365 |
| 2016/0058385 A1 | 3/2016 | Ajima | |
| 2018/0116571 A1* | 5/2018 | Ajima | A61B 5/02 |

FOREIGN PATENT DOCUMENTS

| | | | | |
|---|---|---|---|---|
| EP | 2544124 A1 | 1/2013 | | |
| EP | 3289968 A1 | 3/2018 | | |
| JP | 2002-360530 A | 12/2002 | | |
| JP | 2004-305268 A | 11/2004 | | |
| WO | WO-2016174839 A1 * | 11/2016 | ............... | A61B 5/00 |

* cited by examiner

ELECTRONIC DEVICE AND ESTIMATION SYSTEM

CROSS-REFERENCE TO RELATED APPLICATION

This application claims priority to and benefit of Japanese Patent Application No. 2016-127509 filed on Jun. 28, 2016, the entire contents of which are incorporated herein by reference.

TECHNICAL FIELD

Embodiments of this disclosure relate generally to an electronic device and a system, and more particularly to an electronic device and an estimation system that estimate a subject's state of health from measured biological information.

BACKGROUND

Conventionally, a subject's (user's) state of health is estimated by measuring a blood component or measuring the blood fluidity. These measurements are made using a blood sample collected from the subject. Further, an electronic device that measures biological information from the measured portion such as a wrist of the subject is known. For example, a known electronic device measures a subject's pulse rate while attached to the subject's wrist.

SUMMARY

An electronic device according to an embodiment includes a sensor, a blood pressure measurement portion and a controller. The sensor acquires a subject's pulse wave. The blood pressure measurement portion measures the subject's blood pressure level. The controller estimates a state of glucose metabolism or lipid metabolism of the subject on the basis of an estimation formula created based on the blood pressure level and the pulse wave, the subject's pulse wave acquired by the sensor and the subject's blood pressure level measured by the blood pressure measurement portion.

An estimation system according to an embodiment includes an electronic device, a sphygmomanometer and an estimation apparatus. The electronic device has a sensor configured to acquire a subject's pulse wave. The sphygmomanometer measures the subject's blood pressure level. The estimation apparatus estimates a state of glucose metabolism or lipid metabolism of the subject on the basis of an estimation formula created based on the blood pressure level and the pulse wave, the subject's pulse wave acquired by the sensor and the subject's blood pressure level measured by the sphygmomanometer.

An estimation system according to an embodiment includes an electronic device and an estimation apparatus. The electronic device has a sensor configured to acquire a subject's pulse wave and a blood pressure measurement portion configured to measure the subject's blood pressure level. The estimation apparatus estimates a state of glucose metabolism or lipid metabolism of the subject on the basis of an estimation formula created based on the blood pressure level and the pulse wave, the subject's pulse wave acquired by the sensor and the subject's blood pressure level measured by the blood pressure measurement portion.

DETAILED DESCRIPTION

Pain is involved in collecting a blood sample, and thus it is difficult for a subject to routinely estimate their own state of health by collecting a blood sample. According to an electronic device and an estimation system of this disclosure, a subject's state of health can be estimated easily.

Embodiments of this disclosure are described below in detail with reference to the drawings.

Embodiment 1

Figure 1:
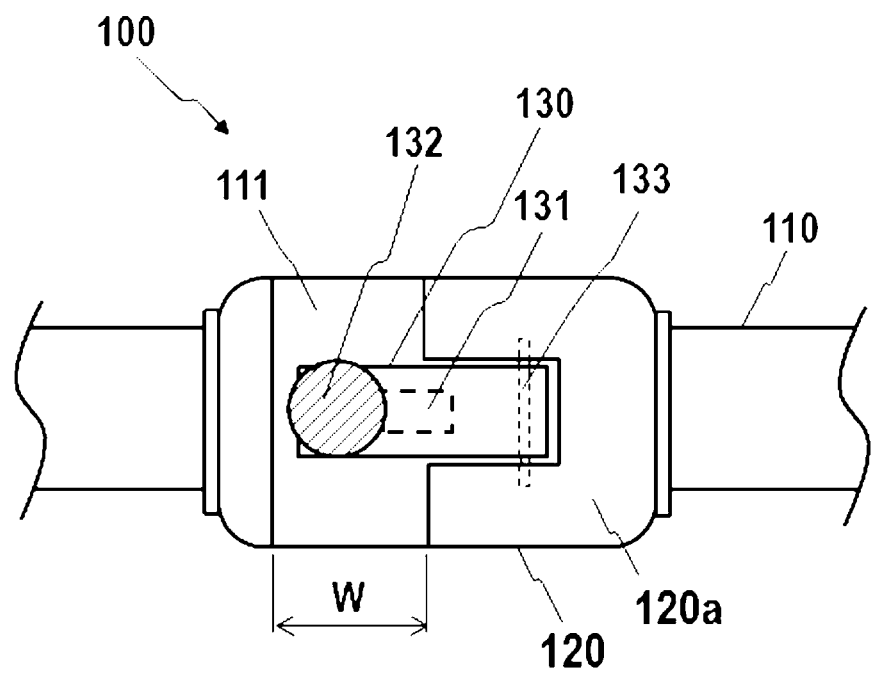
FIG. 1 is a diagram illustrating a schematic configuration of an electronic device according to Embodiment 1.

FIG. 1 is a diagram illustrating a schematic configuration of an electronic device according to Embodiment 1. The electronic device 100 includes a wearing portion 110 and a measurement portion 120. FIG. 1 is a view of the electronic device 100 from a back face 120a that comes in contact with a subject.

The electronic device 100 measures the subject's biological information while the electronic device 100 is worn by the subject. The biological information measured by the electronic device 100 includes the subject's pulse wave. In an embodiment, the electronic device 100 may be worn on the subject's wrist and acquire a pulse wave.

In an embodiment, the wearing portion 110 is a straight, elongated band. Measurement of the pulse wave is performed, for example, in a state in which the subject has wrapped the wearing portion 110 of the electronic device 100 around the wrist. In greater detail, the subject wraps the wearing portion 110 around the wrist so that the back face 120a of the measurement portion 120 is in contact with the measured part and then measures the pulse wave. The electronic device 100 measures the pulse wave of blood flowing through the ulnar artery or the radial artery of the subject.

Figure 2:
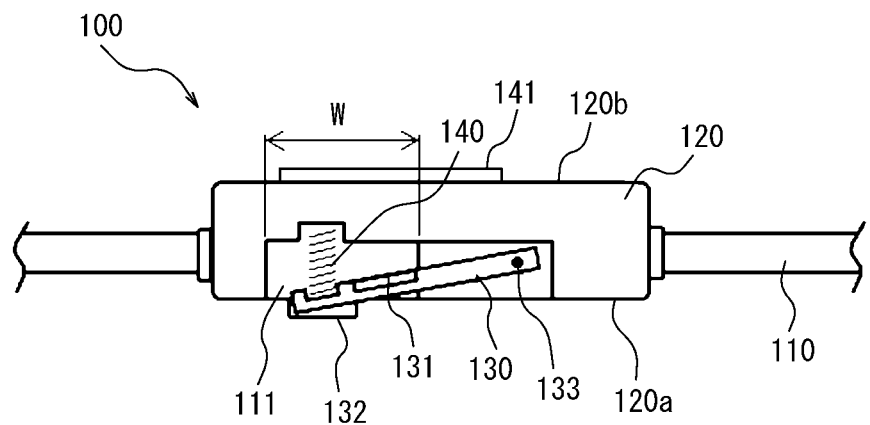
FIG. 2 is a cross-sectional diagram illustrating a schematic configuration of the electronic device in FIG. 1.

FIG. 2 is a cross-sectional diagram of the electronic device 100. FIG. 2 illustrates the measurement portion 120 and the wearing portion 110 around the measurement portion 120.

The measurement portion 120 has the back face 120a which comes in contact with the subject's wrist when worn and a front face 120b on an opposite side from the back face 120a. The measurement portion 120 includes an opening 111 in the back face 120a side. The sensor 130 has a first end that comes in contact with the subject's wrist and a second end that comes in contact with the measurement portion 120 when worn. In a state in which an elastic body 140 is not compressed, the first end protrudes from the opening 111 on the back face 120a side. The first end of the sensor 130 has a pulse pad 132. The first end of the sensor 130 is displaceable in a direction nearly perpendicular to the plane of the back face 120a. The second end of the sensor 130 is in contact with the measurement portion 120 via a shaft 133.

The first end of the sensor 130 is in contact with the measurement portion 120 via the elastic body 140. The first end of the sensor 130 is displaceable relative to the measurement portion 120. The elastic body 140 includes, for example, a spring. The elastic body 140 is not limited to a spring, and may be any other elastic body such as resin or sponge.

A controller, memory, communication interface, power source, notification interface, circuit for causing these components to operate, cable for connecting these components, and the like may be disposed in the measurement portion 120.

The sensor 130 includes an angular velocity sensor 131 that detects displacement of the sensor 130. The angular velocity sensor 131 detects an angular displacement of the sensor 130. The sensor provided in the sensor 130 is not limited to the angular velocity sensor 131 and may, for example, be an acceleration sensor, an angle sensor, or some other type of motion sensor, or a plurality of these sensors.

The electronic device 100 includes an input interface 141 on the front face 120b side of the measurement portion 120. The input interface 141 receives operation input by the subject, and includes, for example, operation buttons (operation keys). Alternatively, the input interface 141 may include, for example, a touch screen.

Figure 3:
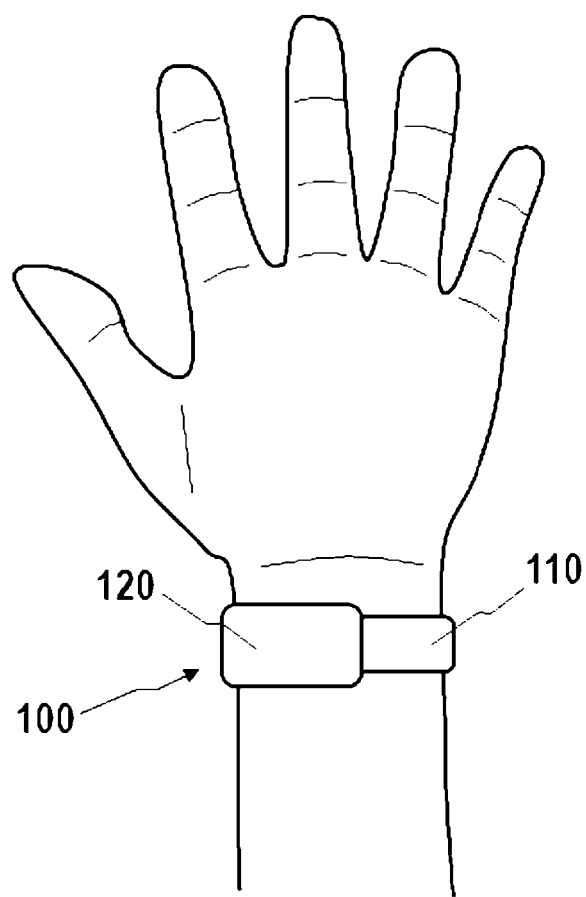
FIG. 3 is a diagram illustrating an example of the electronic device in FIG. 1 being in use.

FIG. 3 is a diagram illustrating an example of the electronic device 100 being used by a subject. The subject wraps the electronic device 100 around the wrist for use. The electronic device 100 is worn so that the back face 120a of the measurement portion 120 is in contact with the wrist. The position of the measurement portion 120 can be adjusted so that the pulse pad 132 is in contact with the position of the ulnar artery or the radial artery while the electronic device 100 is wrapped around the wrist.

In FIG. 3, while the electronic device 100 is worn, the first end of the sensor 130 is in contact with the skin above the radial artery, which is the artery on the thumb side of the subject's left hand. The first end of the sensor 130 is in contact with the skin above the subject's radial artery as a result of the elastic force applied by the elastic body 140 which is arranged between the measurement portion 120 and the sensor 130. The sensor 130 is displaced in accordance with the movement of the subject's radial artery, i.e., pulsation. The angular velocity sensor 131 acquires the pulse wave by detecting displacement of the sensor 130. The pulse wave refers to a waveform representation of the temporal change in volume of a blood vessel due to inflow of blood, acquired from the body surface.

Referring again to FIG. 2, in a state in which the elastic body 140 is not being compressed, the first end of the sensor 130 protrudes from the opening 111. When the electronic device 100 is worn on the subject, the first end of the sensor 130 is in contact with the skin above the subject's radial artery, and in accordance with pulsation, the elastic body 140 expands and contracts, and the first end of the sensor 130 is displaced. A component with an appropriate elastic modulus is used for the elastic body 140 so as to allow it to expand and contract in accordance with pulsation without inhibiting pulsation. The opening width W of the opening 111 is greater than the vessel diameter, i.e., the radial artery diameter in an embodiment. By providing the opening 111 in the measurement portion 120, the back face 120a of the measurement portion 120 does not compress the radial artery when the electronic device 100 is worn. Therefore, the electronic device 100 can acquire a pulse wave with little noise, and thus the measurement accuracy is improved.

FIG. 3 illustrates an example in which the electronic device 100 is worn on the wrist and acquires a pulse wave at the radial artery. However, for example, the electronic device 100 may acquire the pulse wave of blood flowing through a carotid artery in the subject's neck. In greater detail, the subject may press the pulse pad 132 lightly against the position of the carotid artery to measure the pulse wave. The subject may also wrap the electronic device 100 around the neck so that the pulse pad 132 is at the position of the carotid artery.

Figure 4:
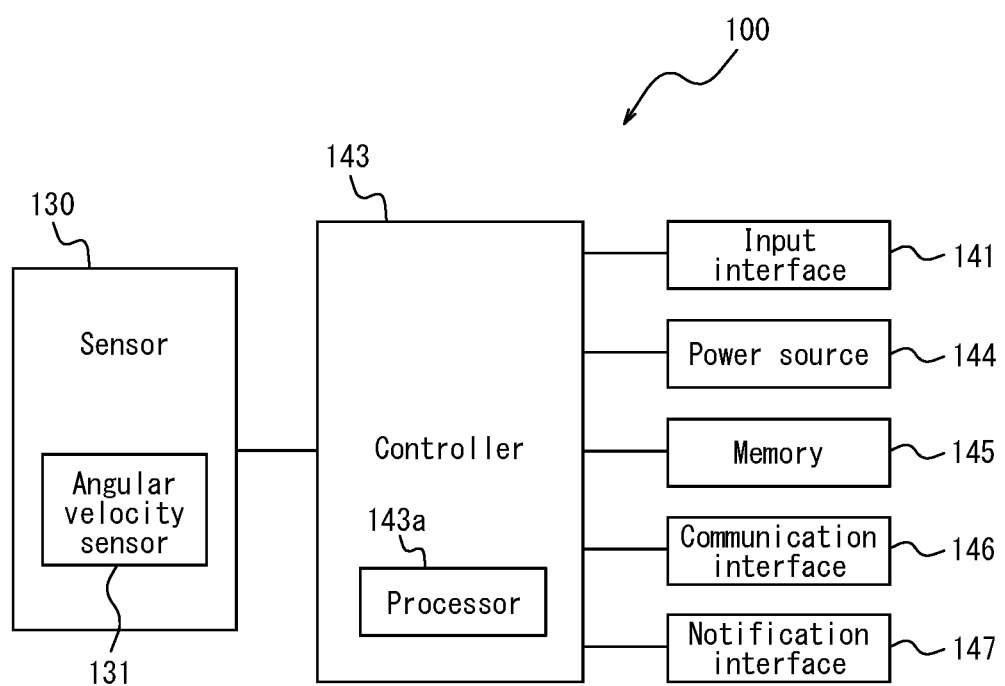
FIG. 4 is a functional block diagram of the electronic device in FIG. 1.

FIG. 4 is a functional block diagram of the electronic device 100. The electronic device 100 includes the sensor 130, the input interface 141, a controller 143, a power source 144, a memory 145, a communication interface 146 and a notification interface 147. In an embodiment, the controller 143, the power source 144, the memory 145, the communication interface 146 and the notification interface 147 may be included in the measurement portion 120 or the wearing portion 110.

The sensor 130 includes the angular velocity sensor 131, detects pulsation from the measured part, and acquires the pulse wave.

The controller 143 is a processor for overall control and management of the electronic device 100, including each functional block of the electronic device 100. The controller 143 is a processor configured to estimate a subject's blood glucose level on the basis of the acquired pulse wave. The controller 143 includes a processor such as a central processing unit (CPU) that executes a program prescribing control procedures and a program that estimates a subject's blood glucose level. These programs are, for example, stored in a storage medium such as the memory 145. In accordance with the index calculated from the pulse wave, the controller 143 estimates a state related to the subject's glucose metabolism, lipid metabolism, or the like. The controller 143 may also notify the notification interface 147 of data.

In the electronic device 100, the controller 143 may include at least one processor 143a so that control and processing capability for executing a variety of functions is provided, as further described in detail below.

According to a variety of embodiments, at least one processor 143a may be executed as a single integrated circuit (IC) or as a plurality of communicably connected ICs and/or discrete circuits. At least one processor 143a can be executed in accordance with a variety of known technologies.

In an embodiment, the processor 143a includes at least one circuit or unit configured to execute at least one data calculation procedure or process by executing an instruction stored in the related memory, for example. In the other embodiments, the processor 143a may be a firmware (e.g. discrete logistic component) that is configured to execute at least one data calculation procedure or process.

According to a variety of embodiments, the processor 143a may include at least one processor, controller, microprocessor, microcontroller, application specific integrated circuit (ASIC), digital signal processor, programmable logistic device, field programmable gate array, any combination of these devices or configurations, or combination of other known devices and configurations, and execute the functions described below.

The power source 144, for example, includes a lithium-ion battery and a control circuit for charging and discharging the lithium-ion battery, and supplies power to the electronic device 100 overall. The power source 144 is not limited to a secondary battery such as a lithium-ion battery or the like, and may be a primary battery such as a button battery or the like.

The memory 145 stores programs and data. The memory 145 may include any non-transitory storage medium, such as a semiconductor storage medium and a magnetic storage medium. The memory 145 may also include a plurality of types of storage media. The memory 145 may include a combination of a portable storage medium, such as a memory card, optical disc, or magneto-optical disc, and an apparatus for reading the storage medium. The memory 145 may include a storage device used as a temporal storage area, such as random access memory (RAM). The memory 145 stores a variety of information and/or programs for causing the electronic device 100 to operate, or the like and also functions as a working memory. The memory 145 may, for example, store the measurement result of the pulse wave acquired by the sensor 130.

The communication interface 146 transmits to/receives from a variety of data through wired or wireless communication with an external apparatus. For example, the communication interface 146 communicates with an external apparatus that stores the biological information of the subject to manage the state of health. The communication interface 146 transmits the measurement result of the pulse wave measured by the electronic device 100 and/or the state of health estimated by the electronic device 100 to the external apparatus.

The notification interface 147 provides notification of information by sound, vibration, images, or the like. The notification interface 147 may include a speaker, a vibrator, and a display device. The display device may be, for example, a liquid crystal display (LCD), an organic electro-luminescence display (OELD), or an inorganic electro-luminescence display (IELD). In an embodiment, for example, the notification interface 147 provides notification of the state of the subject's glucose metabolism or lipid metabolism.

In an embodiment, the electronic device 100 estimates a state of glucose metabolism. In an embodiment, the electronic device 100 estimates the blood glucose level as a state of glucose metabolism.

The electronic device 100 estimates the subject's blood glucose level in accordance with estimation formulas created using regression analysis. The electronic device 100 stores, in advance, estimation formulas for estimating the blood glucose level on the basis of pulse wave and blood pressure level in the memory 145, for example. The electronic device 100 estimates the blood glucose level using these estimation formulas. In this specification, the blood pressure level is a numerical value related to the subject's blood pressure, and may include, for example, a maximum blood pressure, a minimum blood pressure or a pulse pressure. The pulse pressure is a difference between the systolic blood pressure (the maximum blood pressure) and the diastolic blood pressure (the minimum blood pressure).

Here, estimation theory related to estimating the blood glucose level on the basis of a pulse wave is described. As a result of an increase in the blood glucose level after a meal, the blood fluidity reduces (viscosity increases), blood vessels dilate, and the amount of circulating blood increases. Vascular dynamics and hemodynamics are determined so as to balance these states. The reduction in blood fluidity occurs, for example, because of an increase in the viscosity of blood plasma or a reduction in the deformability of red blood cells. Dilation of blood vessels occurs for reasons such as secretion of insulin, secretion of digestive hormones, and a rise in body temperature. When blood vessels dilate, the blood pressure decreases, which leads to a change in the pulse pressure. Further, a reduction in blood pressure is suppressed, and thus pulse rate increases. The increase in the amount of circulating blood compensates for blood consumption for digestion and absorption. Changes in vascular dynamics and hemodynamics before and after a meal due to these factors are also reflected in the pulse wave. In this manner, the blood pressure level and the pulse wave change before and after meals. Therefore, the electronic device 100 can acquire the blood pressure level and the pulse wave before and after meals and estimate the blood glucose level on the basis of the change in the acquired blood pressure level and pulse wave.

Estimation formulas for estimating the blood glucose level in accordance with the above estimation theory can be created by performing regression analysis on sample data representing preprandial/postprandial blood pressure levels, blood glucose levels and pulse waves acquired from a plurality of subjects. The subject's blood glucose level can be estimated by applying the created estimation formulas to the subject's pulse wave index at the time of estimation. The estimation formulas are created in particular by performing regression analysis using sample data for which variation in the blood glucose level is close to a normal distribution, and thus the blood glucose level of the subject being tested can be estimated either before or after a meal.

Figure 5:
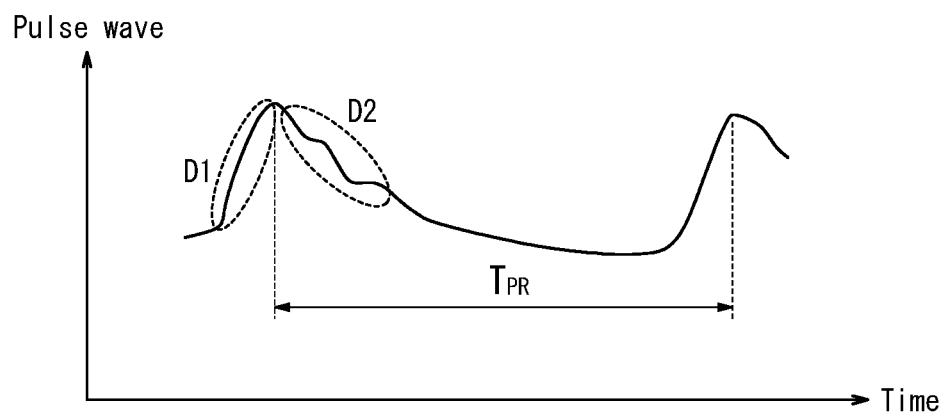
FIG. 5 is a diagram illustrating an example of an estimation method on the basis of change in the pulse wave in the electronic device in FIG. 1.

FIG. 5 is a diagram illustrating an example of an estimation method on the basis of a change in pulse wave and illustrates an example of pulse wave. The estimation formulas for estimating blood glucose level are created using regression analysis with an index based on pulse wave included in an explanatory variable. The index based on pulse wave includes, for example, an index S1 indicating the rising of a pulse wave (rising index), the augmentation index (AI), and the pulse rate (PR).

Figure 6:
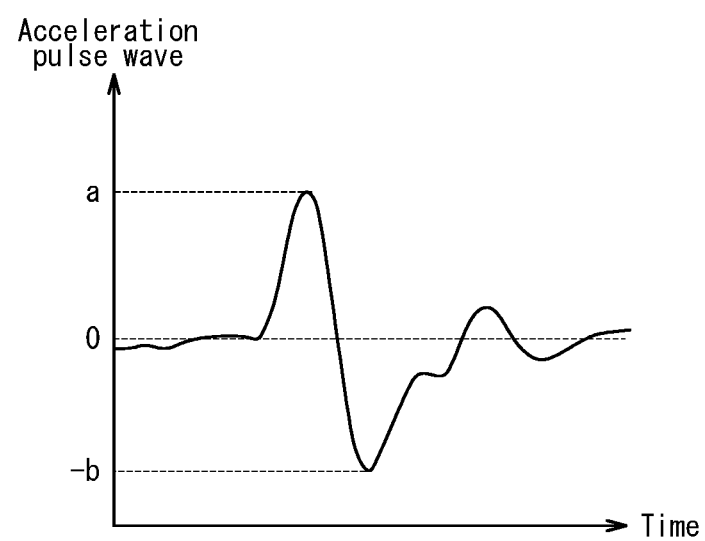
FIG. 6 is a diagram illustrating an example of the acceleration pulse wave.

The rising index S1 is derived using the waveform indicated in the area D1 in FIG. 5. In greater detail, the rising index S1 is the ratio of the first local minimum to the first local maximum in the acceleration pulse wave yielded by the second derivative of the pulse wave. For example, for the acceleration pulse wave illustrated as an example in FIG. 6, the rising index S1 is expressed as $-b/a$. The rising index S1 decreases because of a reduction in fluidity of the blood, secretion of insulin, dilation (relaxation) of blood vessels due to increased insulin secretion and body temperature, or the like after a meal.

Figure 7:
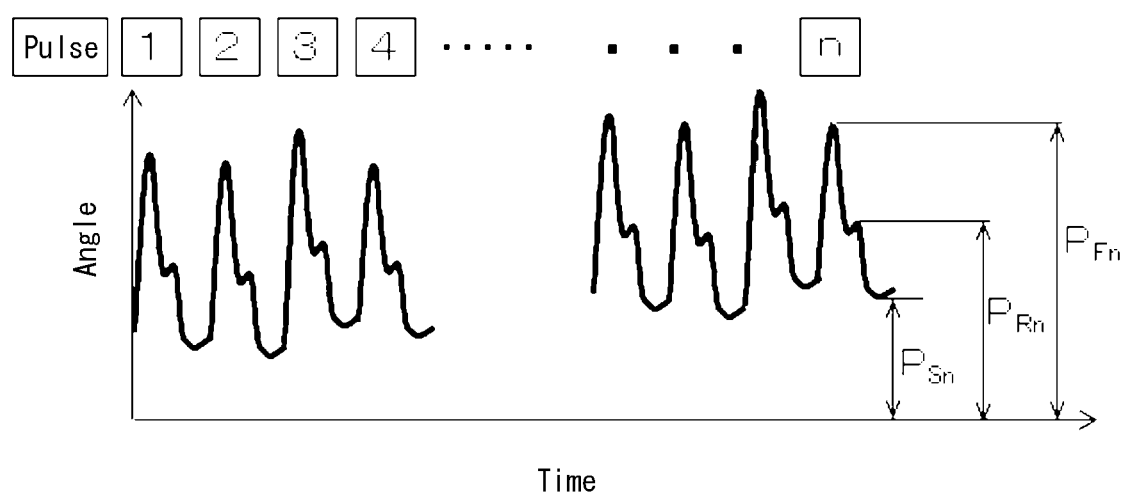
FIG. 7 is a diagram illustrating an example of the pulse wave acquired by a sensor.

AI is an index represented as the ratio between the magnitude of the forward wave and the reflected wave of the pulse wave. A derivative method of AI will be described with reference to FIG. 7. FIG. 7 illustrates an example of pulse waves acquired at the wrist using the electronic device 100. FIG. 7 illustrates the case where the angular velocity sensor 131 is used as the means for detecting the pulsation. FIG. 7 is an integration of the angular velocity acquired by the angular velocity sensor 131. In FIG. 7, the horizontal axis represents time and the vertical axis represents the angle. Since the acquired pulse wave may, for example, include noise that is due to body movement of the subject, the pulse wave may be corrected by a filter that removes the direct current (DC) component, so as to extract only the pulsation component.

Propagation of the pulse wave is a phenomenon in which pulsation due to blood being pumped from the heart is transmitted through artery walls or blood. The pulsation due to blood pumped from the heart reaches the peripheries of limbs as a forward wave, a portion of which is reflected at locations such as where a blood vessel branches, or where the diameter of a blood vessel changes, and returns as a reflected wave. AI is the result of dividing the magnitude of the reflected wave by the magnitude of the forward wave and is represented as $AI_n=(P_{Rn}-P_{Sn})/(P_{Fn}-P_{Sn})$. Here, $AI_n$ is the AI for each pulse beat. AI may, for example, be calculated by measuring the pulse wave for several seconds and calculating the average $AI_{ave}$ of the $AI_n$ for each pulse beat (n=an integer from 1 to n). The AI is derived from the waveform indicated in area D2 of FIG. 5. The AI reduces because of a reduction in fluidity of the blood, dilation of blood vessels due to increased body temperatures, or the like.

The pulse rate PR is derived from the period TPR of the pulse wave illustrated in FIG. 5. The pulse rate PR rises after a meal.

The electronic device 100 can estimate the blood glucose level by the estimation formulas created using the rising index S1, the AI and the pulse rate PR and the blood pressure level measured by using a sphygmomanometer. As a sphygmomanometer, any sphygmomanometers such as those using oscillometric method, Riva-Rocci Korotkoff method and the like may be used.

Figure 8A:
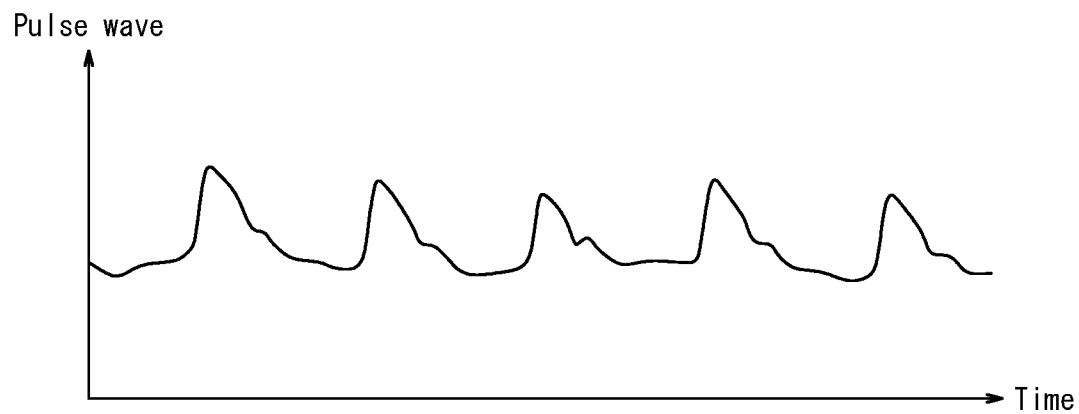
FIGS. 8A and 8B are diagrams illustrating another example of an estimation method on the basis of change in the pulse wave in the electronic device in FIG. 1.
Figure 8B:
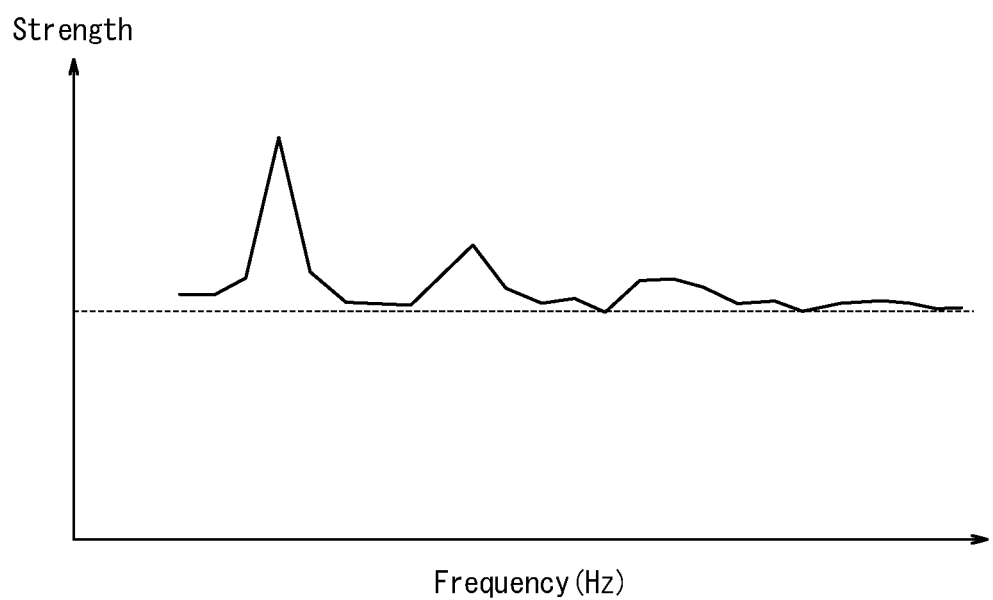

FIGS. 8A and 8B are diagrams illustrating another example of an estimation method based on change in the pulse wave. FIG. 8A illustrates a pulse wave and FIG. 8B illustrates the result of performing a fast Fourier transform (FFT) on the pulse wave in FIG. 8A. The estimation formulas for estimating the blood glucose level are, for example, created by regression analysis related to a fundamental and harmonic wave component (Fourier coefficients) that are derived by the FFT, for example. The peak level in the result of the FFT illustrated in FIG. 8B changes in accordance with the change in the waveform of the pulse wave. Therefore, the blood glucose level can be estimated with estimation formulas created using the Fourier coefficients.

The electronic device 100 estimates the subject's blood glucose level by using the estimation formulas and on the basis of the above described rising index S1, AI, pulse rate PR and pulse pressure, Fourier coefficients and the like.

Here, a method for creating the estimation formulas used in the case where the electronic device 100 estimates the subject's blood glucose level will be described. The estimation formulas may be created by the electronic device 100, or may be created in advance using another computer or the like. In this disclosure, the device that creates the estimation formulas is referred to as estimation formula creation apparatus. The created estimation formulas are, for example, stored in the memory 145 in advance, before the subject estimates the blood glucose level with the electronic device 100.

Figure 9:
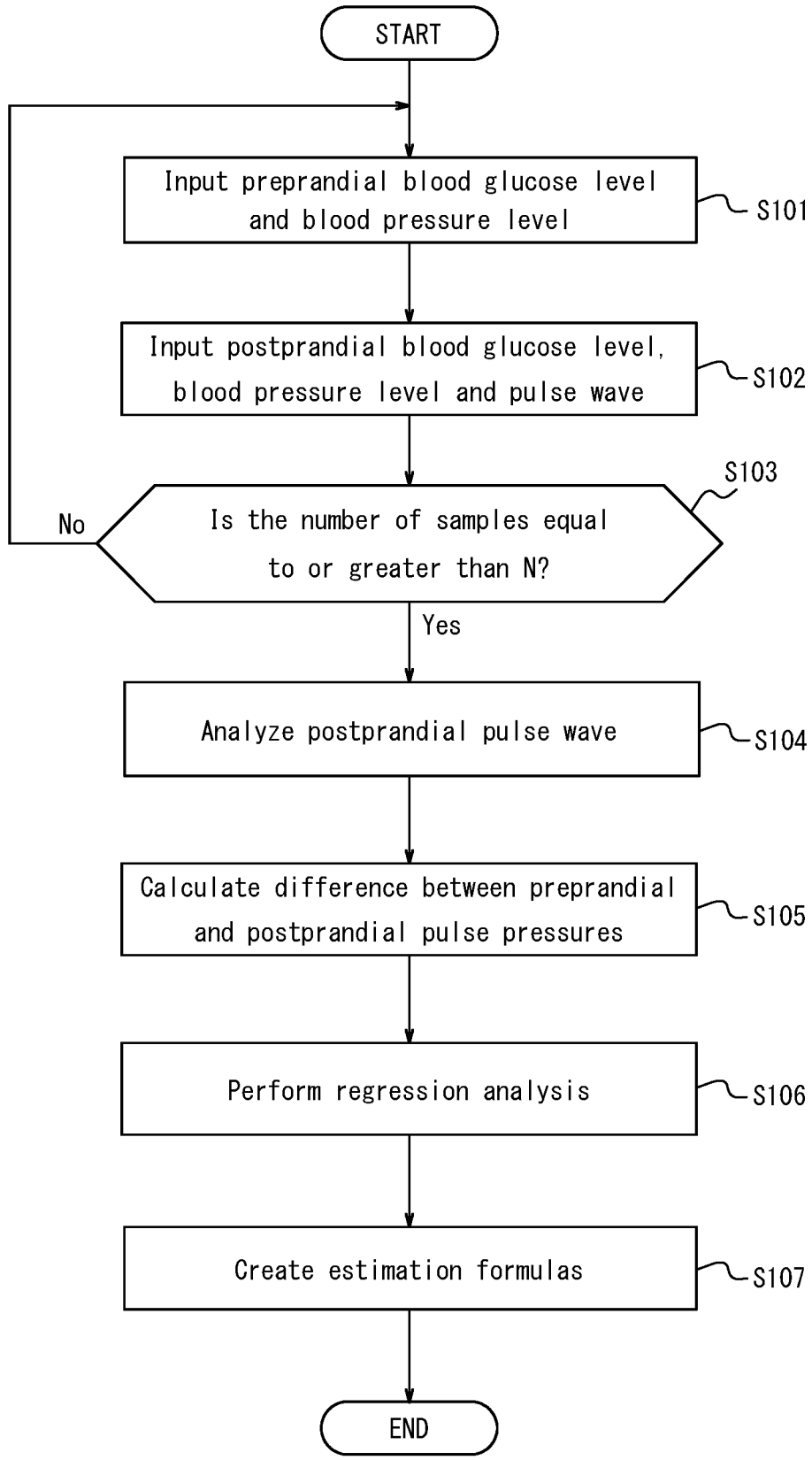
FIG. 9 is a flowchart for creating estimation formulas used by the electronic device in FIG. 1.

FIG. 9 is a flowchart for creating the estimation formulas used by the electronic device 100 in FIG. 1. The estimation formulas are created by performing regression analysis on the basis of the sample data acquired by measuring a subject's preprandial and postprandial blood glucose levels using a blood glucose meter, the subject's blood pressure level using a sphygmomanometer, and the subject's postprandial pulse wave using a pulse wave meter. In this context, preprandial refers to when the subject is fasting, and postprandial refers to the time when the blood glucose level rises after a predetermined length of time elapses after a meal (for example, approximately one hour after the start of the meal). The acquired sample data are not limited to those obtained before and after a meal. It suffices to use data obtained at times with large variation in the blood glucose level.

First, for creation of the estimation formulas, the subject's preprandial blood glucose level and blood pressure level measured respectively by a blood glucose meter and a sphygmomanometer are input into the estimation formula creation apparatus (step S101).

The information on the pulse wave associated with the subject's postprandial blood glucose level, blood pressure level and pulse wave measured respectively using a blood glucose meter, a sphygmomanometer and a pulse wave meter is input into the estimation formula creation apparatus (step S102). The blood glucose levels input in steps S101 and S102 are measured using a blood glucose meter by collecting a blood sample. In steps S101 or S102, the age of the subject of the sample data is also input.

The estimation formula creation apparatus determines whether the number of samples in the sample data input in steps S101 and S102 is equal to or greater than the number of samples, N, sufficient for regression analysis (step S103). The number of samples, N, may be determined as appropriate, and may be 100, for example. When it is determined that the number of samples is fewer than N (in case of "No"), the estimation formula creation apparatus repeats steps S101 and S102 until the number of samples becomes equal to or greater than N. Conversely, when it is determined that the number of samples is greater than or equal to N (in case of "Yes"), the estimation formula creation apparatus proceeds to step S104 and calculates the estimation formulas.

During calculation of the estimation formulas, the estimation formula creation apparatus analyzes the input postprandial pulse wave (step S104). In an embodiment, the estimation formula creation apparatus analyzes the postprandial pulse wave rising index S1, AI and pulse rate PR.

The estimation formula creation apparatus may perform FFT analysis as an analysis of pulse wave.

The estimation formula creation apparatus calculates preprandial and postprandial pulse pressures on the basis of the input preprandial and postprandial blood pressure levels, and calculates a difference between preprandial and postprandial blood pressure levels (DP: difference in pulse pressure) (step S105).

The estimation formula creation apparatus performs regression analysis (step S106). The objective variable in the regression analysis is the preprandial and postprandial blood glucose levels. The explanatory variables in the regression analysis are, for example, the age input in step S101 or S102, the postprandial pulse wave rising index S1, AI, and pulse rate PF analyzed in step S104 and the difference in pulse pressures, DP, calculated in step S105. When the estimation formula creation apparatus performs FFT analysis in step S104, the explanatory variable may be Fourier coefficients calculated as a result of FFT analysis, for example.

The estimation formula creation apparatus creates estimation formulas for estimating the preprandial and postprandial blood glucose level on the basis of the result of the regression analysis (step S106). An example of estimation formulas for estimating the preprandial and postprandial blood glucose levels is indicated below by Formulas (1) and (2).

$$GLa = 1151.9 + 2.79 \times age + 5.27 \times DP - 0.25 \times PRa - 3.69 \times AIa + 6.07 \times S1a \quad (1)$$

$$GLb = 52.7 + 1.75 \times age + 3.28 \times DP + 2.52 \times PRa - 2.59 \times AIa + 1.03 \times S1a \quad (2)$$

In Formulas (1) and (2), GLa is the postprandial blood glucose level and GLb is the preprandial blood glucose level. PRa is the postprandial pulse rate PR, AIa is the postprandial AI and S1a is the postprandial rising index S1.

Next, the estimation process of the blood glucose level by the electronic device 100 using the estimation formulas calculated as described above will be explained. The blood pressure level used by the electronic device 100 for estimating the blood glucose level is input, for example by the subject to the electronic device 100 by measuring the subject's own blood pressure level using a sphygmomanometer. When the electronic device 100 is configured integrally with a sphygmomanometer, that is, when the electronic device 100 has a blood pressure level measuring function, the electronic device 100 performs the estimation process of the blood glucose level using the blood pressure level measured by the subject using the electronic device 100. Here, an example where the electronic device 100 is integral with a sphygmomanometer is explained.

Figure 10:
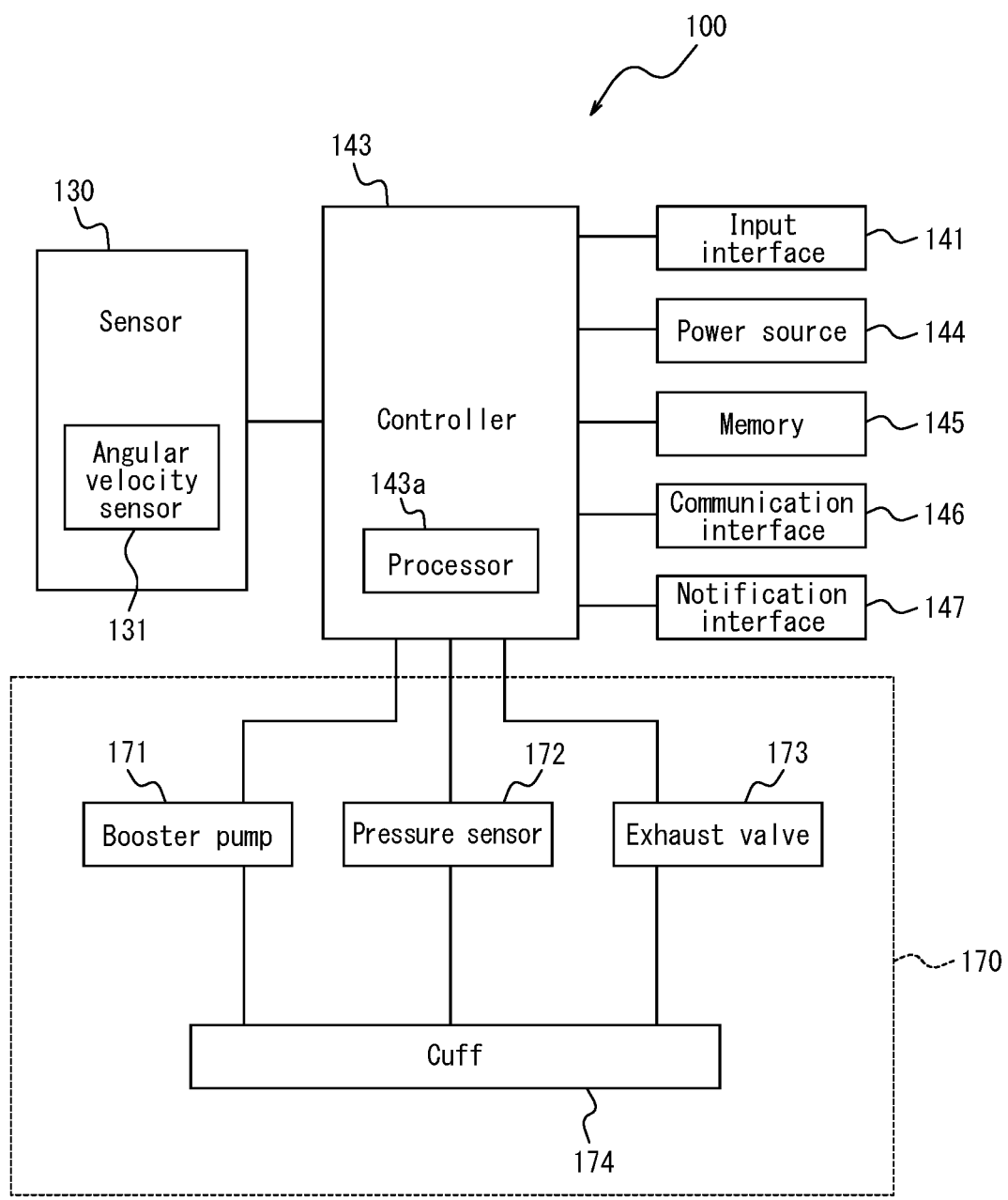
FIG. 10 is a functional block diagram illustrating an example of a schematic configuration of the electronic device having a blood pressure level measurement function.

FIG. 10 is a functional block diagram illustrating an example of the electronic device 100 having a blood pressure level measuring function. The electronic device 100 illustrated in FIG. 10 is an example having a blood pressure level measuring function of what is called a cuff-type sphygmomanometer. In addition to each functional portion as illustrated in FIG. 4, the electronic device 100 further includes a booster pump 171, a pressure sensor 172, an exhaust valve 173 and a cuff 174. The blood pressure measurement portion 170 measures the subject's blood pressure level. The blood pressure measurement portion 170 includes the booster pump 171, the pressure sensor 172, the exhaust valve 173 and the cuff 174.

The booster pump 171 is connected to the cuff 174 via air tube. The subject may wrap the cuff 174 around the arm (upper arm), the wrist or the finger. The cuff 174 is a band of a predetermined width, and includes an air bag into which air can be introduced. The booster pump 171 can supply air to the air bag with the cuff 174 being wrapped around the arm, the wrist or the finger of the subject. When the air is supplied to the air bag, the arm, the wrist or the finger of the subject is fastened by the cuff 174 and the blood vessel is compressed.

The pressure sensor 172 detects the pressure in the air bag of the cuff 174, and outputs a signal related to the detected pressure to the controller 143. The pressure sensor 172 may be disposed on the inside of the cuff 174, for example.

The exhaust valve 173 is connected to the cuff 174 via the air tube. The exhaust valve 173 exhausts the air in the air bag of the cuff 174 to outside.

The booster pump 171 and the exhaust valve 173 are controlled by the controller 143 on the basis of the pressure in the air bag obtained by the pressure sensor 172. The electronic device 100 adjusts the pressure in the air bag of the cuff 174 and measures the subject's blood pressure level with a conventional well-known method.

Figure 11:
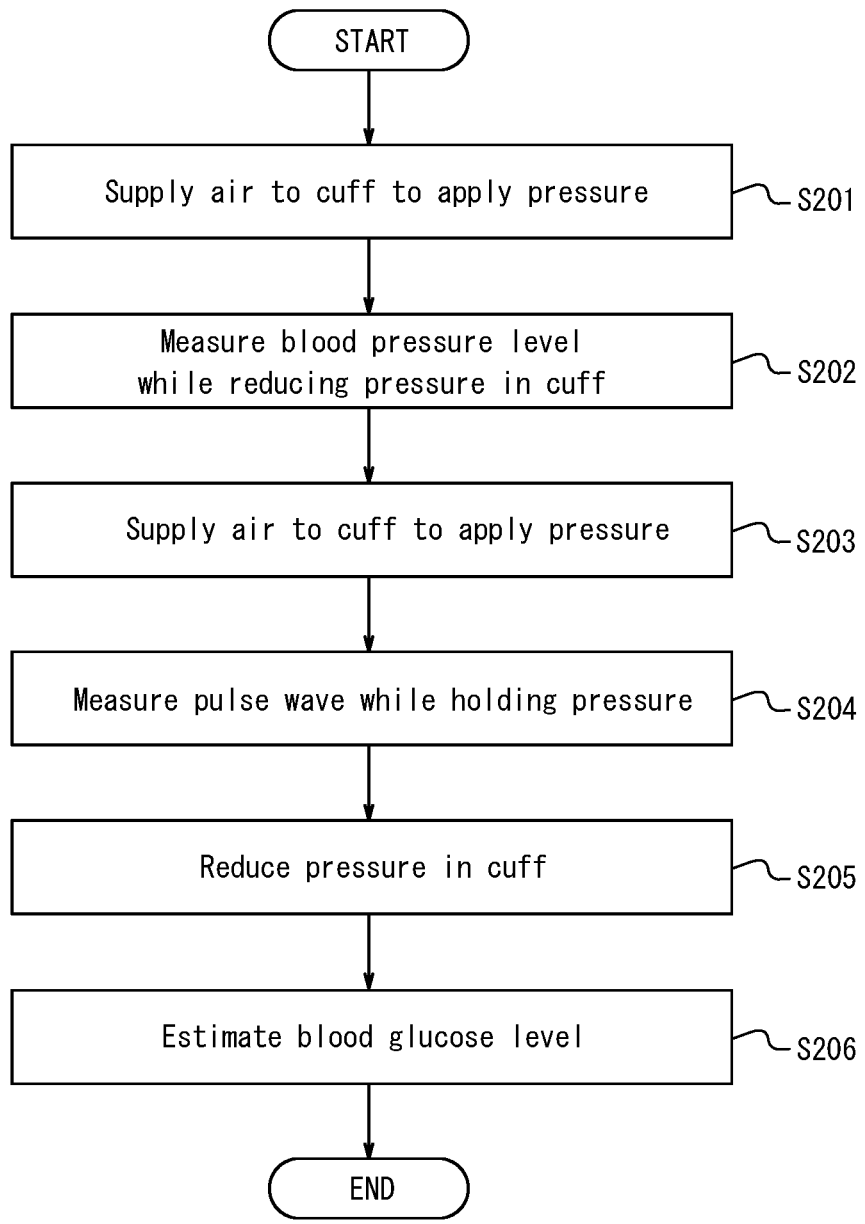
FIG. 11 is a flowchart illustrating an example of a process for estimating a blood glucose level by the electronic device in FIG. 10.

FIG. 11 is a flowchart illustrating an example of the estimation process of the blood glucose level by the electronic device 100 of FIG. 10. The flowchart illustrated in FIG. 11 is started when the subject wearing the cuff 174 performs a specific input operation to the electronic device 100 after a meal.

When the electronic device 100 receives the above described specific input operation by the subject, it supplies air to the air bag of the cuff 174 by the booster pump 171 to apply pressure to the arm, the wrist and the finger of the subject (step S201).

The electronic device 100 measures the subject's blood pressure level by a conventional known method while reducing pressure in the cuff 174 by exhausting the air in the air bag of the cuff 174 through the exhaust valve 173 (step S202). In this manner, the electronic device 100 can acquire the subject's postprandial blood pressure level.

The electronic device 100 again supplies air to the air bag of the cuff 174 by the booster pump 171 to apply pressure to the arm, the wrist and the finger of the subject (step S203). The pressure at this time may be a specific pressure at which the electronic device 100 can acquire a pulse wave, for example, and may be a pressure that is higher than the subject's maximum blood pressure by a specific level (e.g. 35 mmHg), for example. This pressure may be a pressure at which a pulse wave can be stably acquired.

The electronic device 100 holds the pressure of the cuff 174 constant and measures the subject's pulse wave (S204). In this manner, the electronic device 100 can acquire the subject's postprandial pulse wave.

When measurement of the pulse wave is finished, the electronic device 100 reduces the pressure in the cuff 174 by exhausting the air in the air bag of the cuff 174 through the exhaust valve 173 (step S205).

The electronic device 100 estimates the blood glucose level using the estimation formulas (step S206).

The flowchart illustrated in FIG. 11 indicates that the electronic device 100 acquires the pulse wave after acquiring the blood pressure level. However, it is not necessary for the electronic device 100 to perform the process in this order. For example, the electronic device 100 may hold a constant pressure during reduction of the pressure after applying pressure to the arm, the wrist and the finger of the subject in step S201 so as to acquire the pulse wave as illustrated in step S204. In this case, after acquiring the pulse wave, the electronic device 100 starts again reducing the pressure of the cuff 174. When the process is performed in this order, the electronic device 100 can acquire a pulse wave during acquisition of a blood pressure level, that is, between measuring of the maximum pressure and measuring of the minimum pressure. When a pulse wave is acquired, if the pulse wave can be acquired without applying a pressure by the cuff 174, it is not necessary to apply pressure by the cuff 174.

Figure 12:
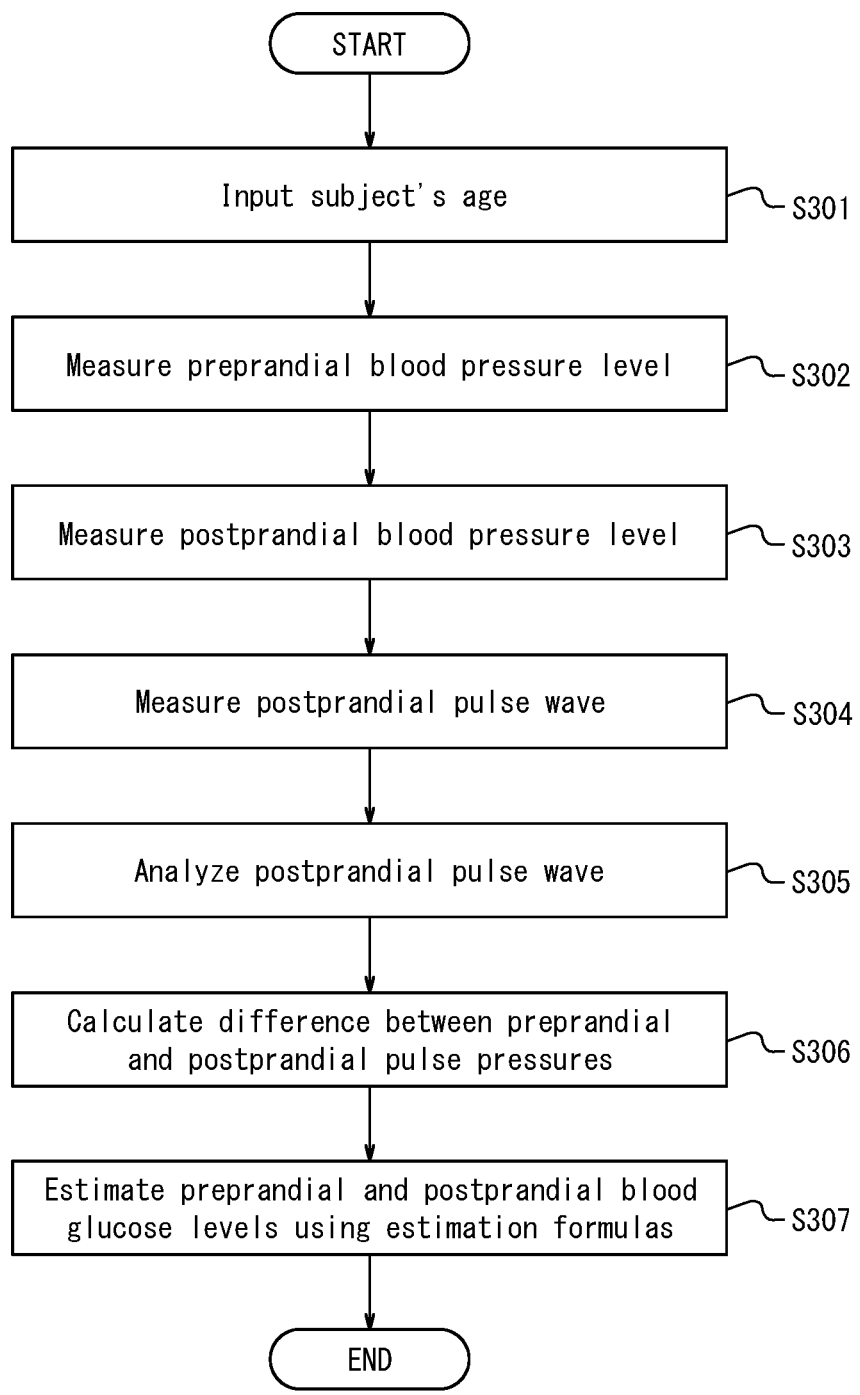
FIG. 12 is a flowchart for estimating preprandial and postprandial blood glucose levels of the subject using estimation formulas created by the flow in FIG. 9.

Next, a process for estimating the subject's blood glucose level using the estimation formulas is described. FIG. 12 is a flowchart for estimating the subject's preprandial and postprandial blood glucose levels using the estimation formulas created according to the flow illustrated in FIG. 9. Here, a process performed by the electronic device 100 having a blood pressure level measuring function as illustrated with reference to FIG. 10 will be described.

The electronic device 100 inputs the subject's age on the basis of operation of the input interface 141 by the subject (step S301).

The electronic device 100 measures the subject's preprandial blood pressure level on the basis of operation of the input interface 141 by the subject (step S302).

The electronic device 100 measures the subject's postprandial blood pressure level on the basis of operation of the input interface 141 by the subject (step S303).

The electronic device 100 measures the subject's postprandial pulse wave on the basis of operation by the subject (step S304).

The electronic device 100 analyzes the measured pulse wave (step S305). In greater detail, the electronic device 100 analyzes on the basis of rising SI, AI and pulse rate PR related to the measured pulse wave, for example.

The electronic device 100 calculates the preprandial and postprandial pulse pressures on the basis of the measured preprandial and postprandial blood pressure levels to calculate the difference between preprandial and postprandial pulse pressures, DP (step S306).

The electronic device 100 estimates the subject's preprandial and postprandial blood glucose levels by, for example, substituting the rising index SI, the AI and the pulse rate PR analyzed in step S305, the difference between the preprandial pulse pressure and the postprandial pulse pressure, DP, calculated in step S306, and the age of the subject into Formulas (1) and (2) above (step S307). The subject is notified, for example, of the estimated preprandial and postprandial blood glucose levels by the notification interface 147 of the electronic device 100, for example.

The postprandial blood pressure level (step S303) and the postprandial pulse wave (step S304) may be measured in accordance with the process from the step S201 to the step S205 illustrated in FIG. 11.

When the electronic device 100 does not have the blood pressure level measuring function, the subject inputs a blood pressure measured using a separate sphygmomanometer to the electronic device 100. In this case, the electronic device 100 accepts an input of a blood pressure level by the subject instead of measurement of the subject's blood pressure level in steps S302 and S303.

Figure 13:
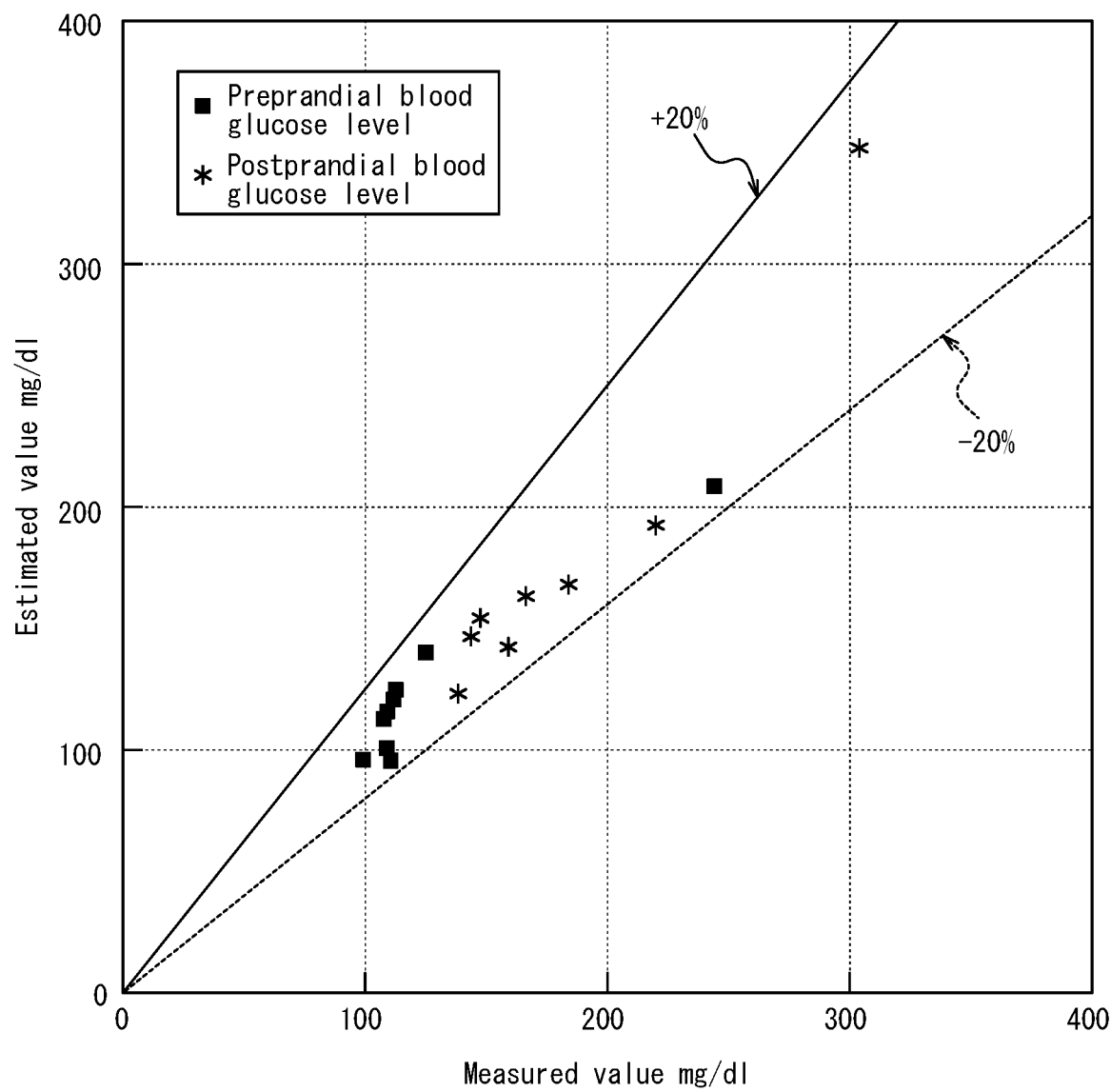
FIG. 13 is a diagram illustrating a comparison between the preprandial and postprandial blood glucose levels estimated using estimation formulas created by the flow in FIG. 9 and measured preprandial and postprandial blood glucose levels.

FIG. 13 illustrates a comparison between the preprandial and postprandial blood glucose levels estimated using the estimation formulas created according to the flow in FIG. 9 and the actual measured preprandial and postprandial blood glucose levels. In the graph illustrated in FIG. 13, the measured level (actual measured level) of the preprandial and postprandial blood glucose levels is indicated on the horizontal axis and the estimated levels thereof are indicated on the vertical axis. The blood glucose level was measured using the blood glucose meter Medisafe Fit manufactured by Terumo Corporation. As illustrated in FIG. 13, the measured levels and the estimated levels are mostly contained within the range of ±20%. In other words, the estimation accuracy with the estimation formulas is considered to be within 20%.

In this manner, the electronic device 100 can estimate the preprandial and postprandial blood glucose levels in a non-invasive manner and in a short time on the basis of the preprandial and postprandial blood pressure levels measured by the subject using a sphygmomanometer. In particular, the AI is a parameter that is dependable on the blood pressure level. Thus, as with the electronic device 100, when the blood glucose level is estimated on the basis of the estimation formulas created by containing blood pressure levels as explanatory variables, the estimation accuracy of the blood glucose level can be improved. In an embodiment, although the estimation formulas are created using preprandial and postprandial blood glucose levels, preprandial and postprandial blood pressure levels and postprandial pulse waves, creation of estimation formulas is not limited thereto, estimation formulas may be created using a postprandial blood glucose level or either preprandial or postprandial blood pressure level and pulse wave. The electronic device 100 may estimate not only preprandial and postprandial blood glucose levels, but also subject's blood glucose level in any timing. The electronic device 100 can estimate a blood glucose level in any timing in a non-invasive manner and in a short time.

The electronic device 100 according to an embodiment may update the estimation formulas stored in the memory 145 on the basis of the subject's preprandial and postprandial blood pressure levels acquired in steps S302 and S303 for estimation of the blood glucose level. In other words, the electronic device 100 can use the preprandial and postprandial blood pressure levels and the postprandial pulse wave acquired for estimating the blood glucose level as sample data for updating the estimation formulas. Thus, the estimation formulas are updated each time the subject estimates a blood glucose level, and the estimation accuracy of preprandial and postprandial blood glucose levels using the estimation formulas is increased.

Embodiment 2

In Embodiment 1, cases where the electronic device 100 estimates the subject's preprandial and postprandial blood glucose levels have been described. In Embodiment 2, an example where the electronic device 100 estimates the subject's state of lipid metabolism is described. In an embodiment, the electronic device 100 estimates the postprandial lipid level as the state of lipid metabolism. The lipid level includes neutral fat, total cholesterol, HDL cholesterol, LDL cholesterol, and the like. Description of points that are similar to those of Embodiment 1 is omitted as appropriate.

The electronic device 100 stores in advance the estimation formulas for estimating the lipid level on the basis of the pulse wave in the memory 145, for example. The electronic device 100 estimates the lipid level using these estimation formulas.

The estimation theory related to estimation of the lipid level based on the pulse wave is similar to the estimation theory for blood glucose level described in Embodiment 1. In other words, a change in the lipid level in the blood is also reflected in a change in the waveform of the pulse wave and a change in the blood pressure level. Thus, the electronic device 100 acquires the blood pressure level and the pulse wave, and can estimate the lipid level on the basis of a change in the acquired blood pressure level and pulse wave.

The electronic device 100 estimates the lipid level using the pulse wave and the blood pressure level when a lipid is estimated, and thus the estimation accuracy of the lipid level is improved.

Figure 14:
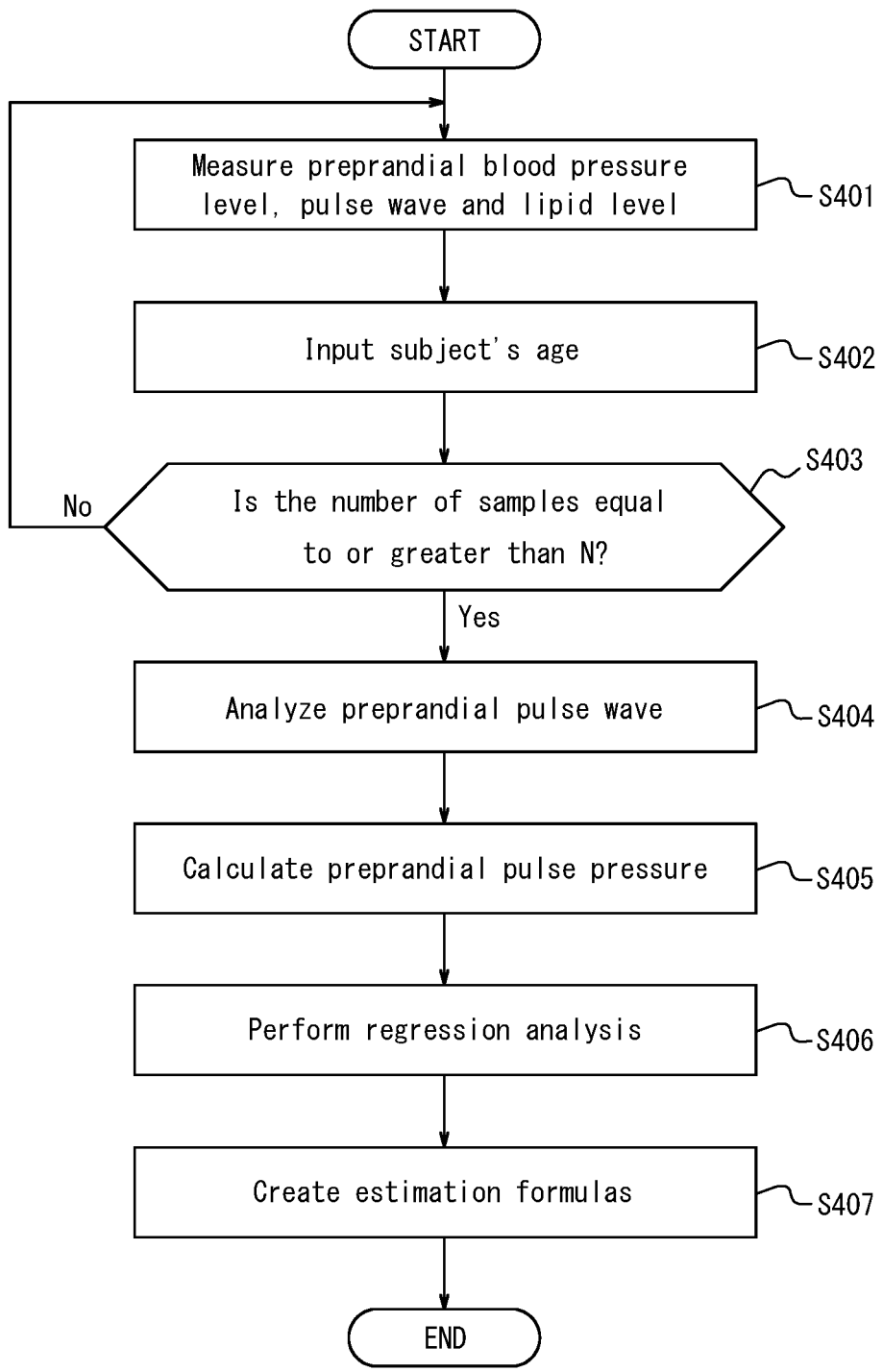
FIG. 14 is a flowchart for creating estimation formulas used by an electronic device according to Embodiment 2.

FIG. 14 is a flowchart for creating estimation formulas used by the electronic device 100 according to an embodiment. In an embodiment, the estimation formulas are created by performing regression analysis on the basis of the sample data. In an embodiment, the estimation formulas are created on the basis of the preprandial pulse wave, lipid level and blood pressure level as the sample data. In an embodiment, preprandial refers to when the subject is fasting, and postprandial refers to the time when the lipid level rises after a predetermined length of time elapses after a meal (for example, approximately three hours after the start of the meal). The estimation formulas are created in particular by performing regression analysis using sample data for which variation in the blood glucose levels is close to a normal distribution, and thus the lipid level of the subject being tested can be estimated at any timing either before or after a meal.

When the estimation formulas are created, the information related to the subject's preprandial blood pressure level, pulse wave and lipid level measured respectively by a sphygmomanometer, a sphygmograph and a lipid measuring apparatus is input to the estimation formula creation apparatus (step S401).

The age of the subject of each sample data is also input to the estimation formula creation apparatus (step S402).

The estimation formula creation apparatus determines whether the number of samples in the sample data input in step S401 and step S402 is equal to or greater than the number of samples, N, sufficient for regression analysis (step S403). The number of samples, N, can be determined as appropriate, and may be 100, for example. When it is determined that the number of samples is fewer than N (in case of "No"), the estimation formula creation apparatus repeats step S401 and step S402 until the number of samples becomes equal to or greater than N. Conversely, when it is determined that the number of samples is greater than or equal to N (in case of "Yes"), the estimation formula creation apparatus proceeds to step S204 and calculates the estimation formulas.

During calculation of the estimation formulas, the estimation formula creation apparatus analyzes the input preprandial pulse wave (step S404). In an embodiment, the estimation formula creation apparatus analyzes preprandial pulse wave's rising index S1, AI and pulse rate PR. The estimation formula creation apparatus may perform FFT analysis as the pulse wave analysis.

The estimation formula creation apparatus calculates the preprandial pulse pressure on the basis of the input preprandial blood pressure level (step S405).

The estimation formula creation apparatus performs regression analysis (step S406). The objective variable in the regression analysis is the preprandial lipid level. The explanatory variable in the regression analysis is the age input in step S502 and the rising index S1, the AI, and the pulse rate PR of the preprandial pulse wave analyzed in step S504 and the preprandial pulse pressure calculated in step S405. When the estimation formula creation apparatus performs FFT analysis in step S404, the explanatory variable may, for example, be the Fourier coefficients calculated as the result of an FFT analysis.

The estimation formula creation apparatus creates estimation formulas for estimating the preprandial lipid level on the basis of the result of the regression analysis (step S407).

Figure 15:
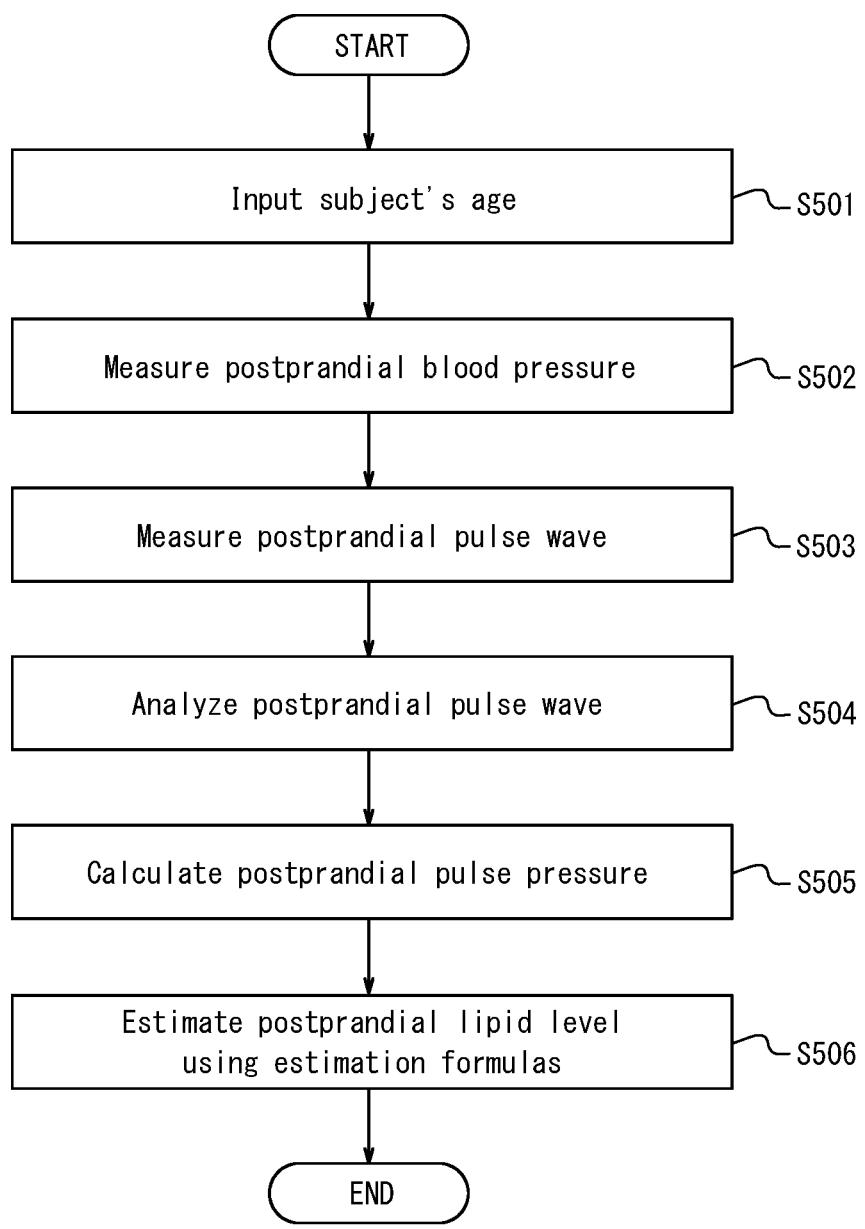
FIG. 15 is a flowchart for estimating a subject's lipid level by using estimation formulas created by the flow in FIG. 14.

Next, a process for estimating the subject's lipid level using estimation formulas is described. FIG. 15 is a flowchart for estimating the subject's lipid level using the estimation formulas created according to the flow in FIG. 14. Here, as described with reference to FIG. 10, the electronic device 100 is explained as the electronic device 100 having a blood pressure level measuring function.

The electronic device 100 inputs a subject's age on the basis of operation of the input interface 141 by the subject (step S501).

The electronic device 100 measures the subject's postprandial blood pressure level on the basis of operation by the subject after a meal (step S502).

The electronic device 100 measures the subject's postprandial pulse wave on the basis of operation by the subject (step S503).

The electronic device 100 analyzes the measured pulse wave (step S504). In greater detail, the electronic device 100 analyzes the rising index S1, the AI and the pulse rate PR related to the measured pulse wave, for example.

The electronic device 100 calculates the postprandial pulse pressure on the basis of the measured postprandial blood pressure level (step S505).

The electronic device 100 estimates the subject's postprandial lipid level by substituting the rising index S1, the AI and the pulse rate PR analyzed in step S504, the postprandial pulse pressure calculated in step S505 and the age of the subject into the estimation formulas created according to the flowchart of FIG. 14 (step S506). The estimated postprandial lipid level is notified, for example, from the notification interface 147 of the electronic device 100 to the subject. The postprandial blood pressure level (step S502) and the postprandial pulse wave (step S503) may be measured according to the process from step S201 to step S205 illustrated in FIG. 11.

In this manner, the electronic device 100 can estimate the postprandial lipid level on the basis of the measured postprandial blood pressure level. The electronic device 100 according to an embodiment estimates the lipid level using the postprandial blood pressure level. In particular, the AI is a parameter that is dependable on the blood pressure level. Thus, as with the electronic device 100, the lipid level is estimated on the basis of the estimation formulas created by containing the blood pressure level as the explanatory variable, thereby improving the estimation accuracy of the lipid level.

The electronic device 100 may estimate, not limited to the postprandial lipid level, a subject's lipid level in any timing. The electronic device 100 can also estimate the lipid level in any timing in a non-invasive manner and in a short time.

As with Embodiment 1, the electronic device 100 according to an embodiment may also update the estimation formulas stored in the memory 145 on the basis of the subject's postprandial blood pressure level and the pulse wave obtained in step S502 for estimating the lipid level. Thus, the estimation formulas are updated each time the subject estimates the lipid level, and the estimation accuracy of the postprandial lipid level using the estimation formulas is increased.

Figure 16:
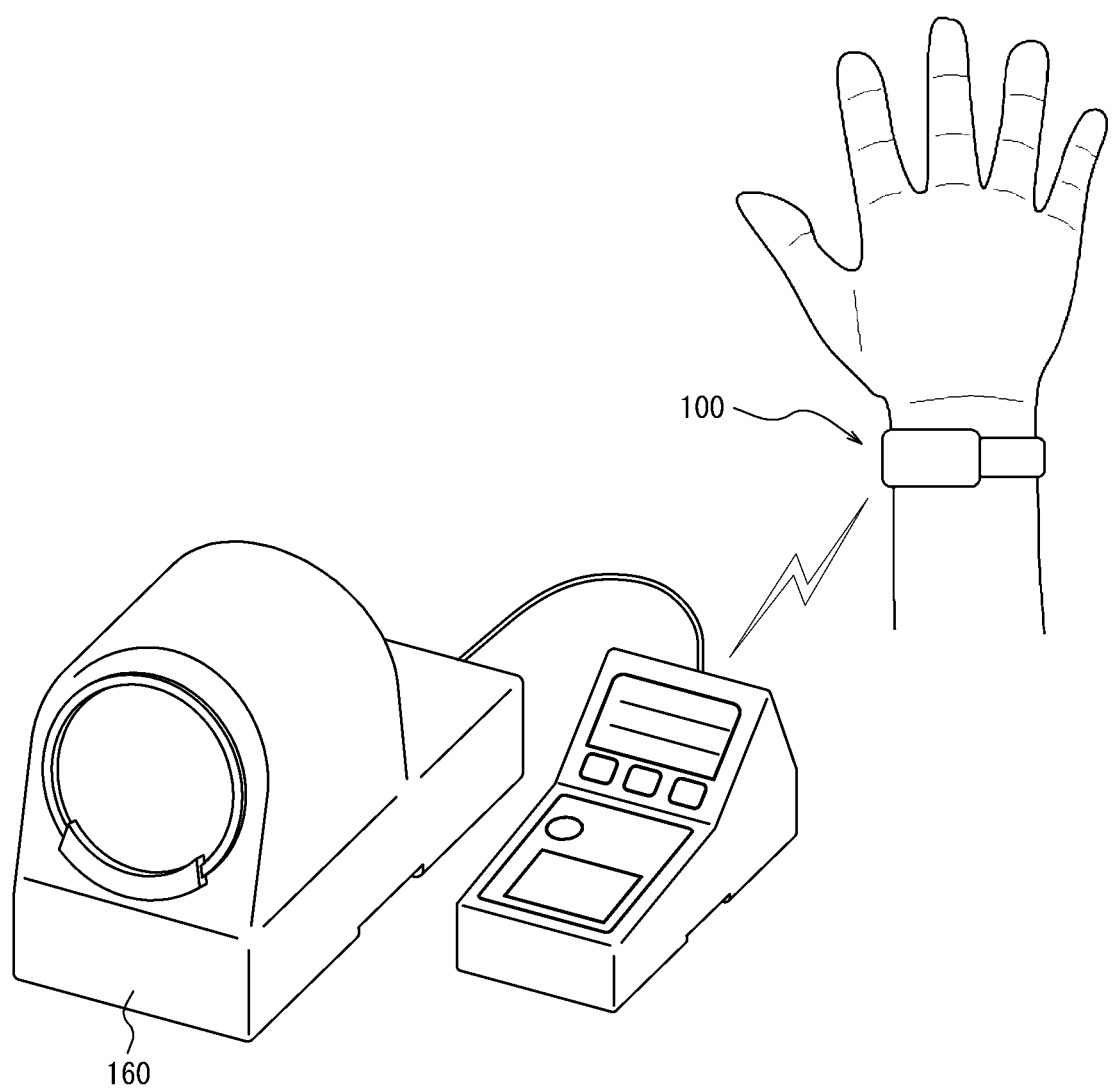
FIG. 16 is a schematic diagram illustrating communication between the electronic device and a sphygmomanometer.

When the electronic device 100 does not have a blood pressure level measuring function, the blood pressure level may be automatically input from the sphygmomanometer to the electronic device 100 as illustrated in FIG. 16, for example.

FIG. 16 is a schematic diagram illustrating communication between the electronic device 100 and the sphygmomanometer 160. The sphygmomanometer 160 includes a communication interface and can transmit/receive information via the communication interface 146 of the electronic device 100. When the sphygmomanometer 160 measures the blood pressure level on the basis of operation by the subject, for example, it transmits the blood pressure level as a measuring result to the electronic device 100. The electronic device 100 uses the blood pressure level acquired from the sphygmomanometer 160 and estimates the preprandial and postprandial blood glucose levels or the postprandial lipid level of the subject in accordance with the flow illustrated in FIG. 12, FIG. 15, or the like.

In the above described embodiment, the blood glucose level or the lipid level is estimated by the electronic device 100. However, estimation of the blood glucose level or the lipid level is not necessarily performed by the electronic device 100. An example of estimating the blood glucose level or the lipid level by an apparatus other than the electronic device 100 will be described.

Figure 17:
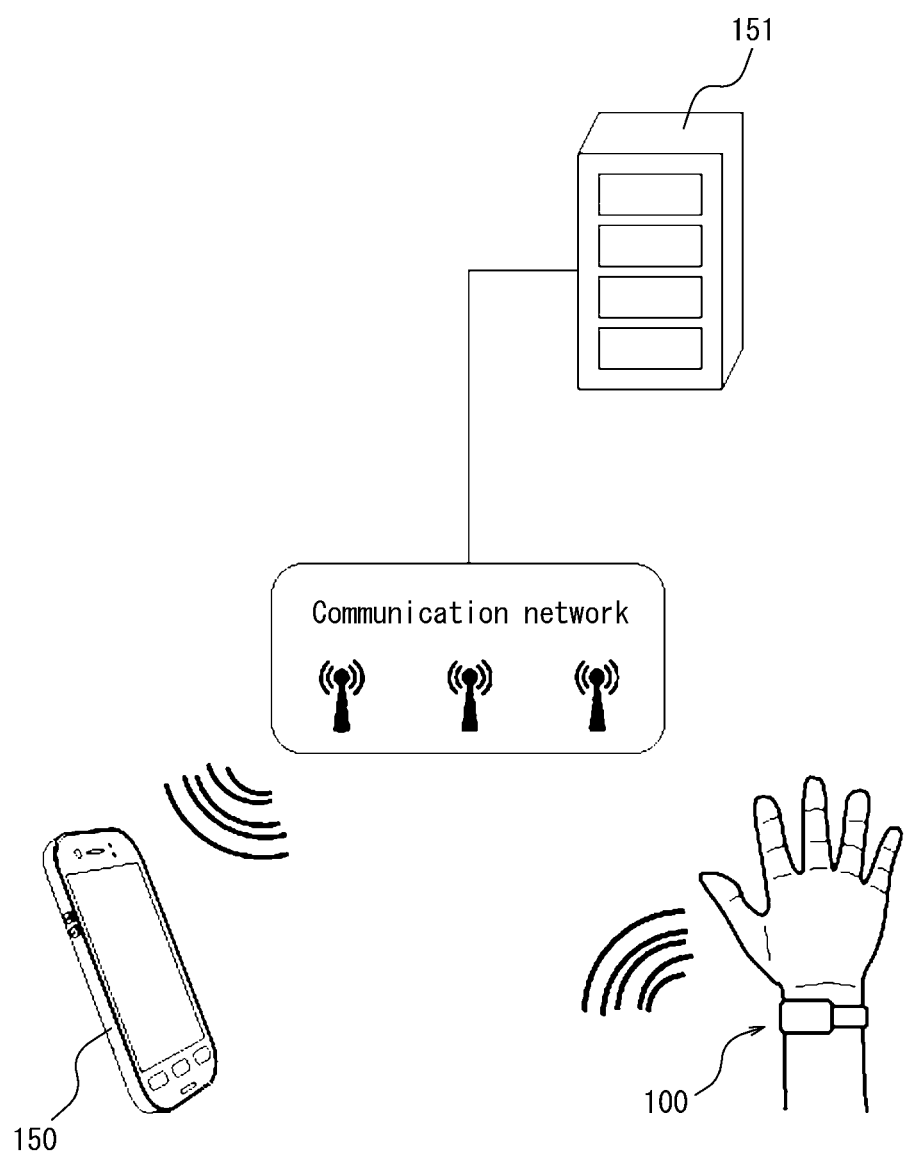
FIG. 17 is a schematic diagram illustrating a schematic configuration of a system according to an embodiment.

FIG. 17 is a diagram illustrating a schematic configuration of a system according to an embodiment. The system according to the embodiment illustrated in FIG. 17 includes the electronic device 100, a server 151, a mobile terminal 150 and a communication network. As illustrated in FIG. 17, the pulse wave measured by the electronic device 100 is transmitted to the server 151 over the communication network and is stored in the server 151 as the personal information of the subject. The server 151 serves as the estimation apparatus that estimates a state of glucose metabolism or lipid metabolism of the subject. The server 151 compares the pulse wave with the information of the subject acquired in the past or a variety of data base and estimates the blood glucose level or the lipid level of the subject. The server 151 may further create appropriate advice for the subject. The server 151 replies to the mobile terminal 150 in the subject's possession with estimation results and advice. The mobile terminal 150 can establish a system to provide notification of received estimation results and advice via the display of the mobile terminal 150. By using the communication function of the electronic device 100, information from a plurality of users can be collected on the server 151. Thus the estimation accuracy is further increased. Further, since the mobile terminal 150 is used as notification means, the electronic device 100 does not require the notification interface 147 and can be further reduced in size. Since the blood glucose level or the lipid level of the subject is estimated by the server 151, the calculation load on the controller 143 of the electronic device 100 can be reduced. Further, since the subject's information acquired in the past can be stored on the server 151, load on the memory 145 of the electronic device 100 can be reduced. Therefore, the electronic device 100 can be further reduced in size and complexity, and the processing speed for calculation is also improved.

In the system according to an embodiment, the electronic device 100 and the mobile terminal 150 are illustrated as connected over the communication network. However, systems according to this disclosure are not limited to this configuration. The electronic device 100 and the mobile terminal 150 may be connected directly over the communication network without use of the server 151.

Some embodiments have been described for a complete and clear disclosure. The appended claims, however, are not limited to the above embodiments and are to be construed as encompassing all of the possible modifications and alternate configurations that a person of ordinary skill in the art could have made within the scope of the fundamental features indicated in this disclosure. Each requirement illustrated in some embodiments can be combined freely.

For example, in the above embodiments, cases where the sensor 130 is provided with the angular velocity sensor 131 has been described. However, the electronic device 100 is not limited to this case. The sensor 130 may be provided with an optical pulse wave sensor constituted by an optical emitter and an optical detector or may be provided with a pressure sensor. The electronic device 100 is not limited to being worn on the wrist. It suffices for the sensor 130 to be placed on an artery, such as on the neck, ankle, thigh, ear, or the like.

The invention claimed is:

1. An electronic device comprising:
a sensor configured to acquire a subject's pulse wave in a non-invasive manner;
a blood pressure measurement portion, including the sensor or a second sensor, configured to measure the subject's blood pressure level in a non-invasive manner;
a controller configured to automatically determine a rising index based on the subject's pulse wave acquired by the sensor, automatically estimate a blood glucose level of the subject on the basis of the determined rising index and the subject's blood pressure level measured by the blood pressure measurement portion; and
a communication interface configured to transmit to an external apparatus the blood glucose level of the subject estimated by the controller in real time, or a notification interface configured to notify the subject of the blood glucose level of the subject estimated by the controller in real time,
wherein the rising index is a ratio of a first local minimum to a first local maximum in an acceleration pulse wave yielded by a second derivative of the subject's pulse wave.

2. The electronic device according to claim 1, wherein the sensor is configured to detect acceleration or angular velocity.

3. The electronic device according to claim 1, wherein the blood pressure measurement portion is a cuff-type sphygmomanometer.

4. The electronic device according to claim 1, wherein the controller estimates the blood glucose level of the subject using an estimation formula created on the basis of the rising index and the blood pressure level, and
the controller updates the estimation formula on the basis of the subject's blood pressure level measured by the blood pressure measurement portion and the subject's pulse wave acquired by the sensor.

5. The electronic device according to claim 1, wherein the sensor acquires the subject's pulse wave while the blood pressure measurement portion measures the subject's blood pressure level.

6. The electronic device according to claim 1, wherein the controller is further configured to:
determine an augmentation index based on the subject's pulse wave acquired by the sensor, and
estimate the blood glucose level on the basis of the determined augmentation index, the determined rising index, and the subject's blood pressure level measured by the blood pressure measurement portion,
wherein the augmentation index is a ratio between a forward wave and a reflected wave of the subject's pulse wave.

7. An estimation system comprising:
an electronic device having a sensor configured to acquire a subject's pulse wave in a non-invasive manner;

a sphygmomanometer configured to measure the subject's blood pressure level in a non-invasive manner;

an estimation apparatus configured to automatically determine a rising index based on the subject's pulse wave acquired by the sensor and automatically estimate a blood glucose level of the subject on the basis of the determined rising index and the subject's blood pressure level measured by the sphygmomanometer; and a communication interface configured to transmit to an external apparatus the blood glucose level of the subject estimated by the controller in real time, or a notification interface configured to notify the subject of the blood glucose level of the subject estimated by the controller in real time, wherein the rising index is a ratio of a first local minimum to a first local maximum in an acceleration pulse wave yielded by a second derivative of the subject's pulse wave.

8. The estimation system according to claim 7, wherein the estimation apparatus is further configured to:

determine an augmentation index based on the subject's pulse wave acquired by the sensor, and estimate the blood glucose level on the basis of the determined augmentation index, the determined rising index, and the subject's blood pressure level measured by the blood pressure measurement portion, wherein the augmentation index is a ratio between a forward wave and a reflected wave of the subject's pulse wave.

9. An estimation system comprising:

an electronic device having a sensor configured to acquire a subject's pulse wave in a non-invasive manner and a blood pressure measurement portion, including the sensor or a second sensor, configured to measure the subject's blood pressure level in a non-invasive manner;

an estimation apparatus configured to automatically determine a rising index based on the subject's pulse wave acquired by the sensor and automatically estimate a blood glucose level of the subject on the basis of the determined rising index and the subject's blood pressure level measured by the blood pressure measurement portion; and a communication interface configured to transmit to an external apparatus the blood glucose level of the subject estimated by the controller in real time, or a notification interface configured to notify the subject of the blood glucose level of the subject estimated by the controller in real time, wherein the rising index is a ratio of a first local minimum to a first local maximum in an acceleration pulse wave yielded by a second derivative of the subject's pulse wave.

10. The estimation system according to claim 9, wherein the estimation apparatus is further configured to:

determine an augmentation index based on the subject's pulse wave acquired by the sensor, and estimate the blood glucose level on the basis of the determined augmentation index, the determined rising index, and the subject's blood pressure level measured by the blood pressure measurement portion, wherein the augmentation index is a ratio between a forward wave and a reflected wave of the subject's pulse wave.

* * * * *